(12) United States Patent
Rombach

(10) Patent No.: US 9,713,526 B2
(45) Date of Patent: Jul. 25, 2017

(54) TWO OPTICAL ELEMENTS WHICH, IN COMBINATION, FORM A LENS OF VARIABLE OPTICAL POWER FOR APPLICATION AS AN INTRAOCULAR LENS

(75) Inventor: Michiel Christiaan Rombach, Breda (NL)

(73) Assignee: Akkolens International B.V., Breda (NL)

( * ) Notice: Subject to any disclaimer, the term of this patent is extended or adjusted under 35 U.S.C. 154(b) by 2011 days.

(21) Appl. No.: 10/589,320

(22) PCT Filed: Mar. 1, 2005

(86) PCT No.: PCT/NL2005/000153
§ 371 (c)(1),
(2), (4) Date: May 23, 2007

(87) PCT Pub. No.: WO2005/084587
PCT Pub. Date: Sep. 15, 2005

(65) Prior Publication Data
US 2008/0046076 A1    Feb. 21, 2008

(30) Foreign Application Priority Data
Mar. 3, 2004    (NL) ...................................... 1025622

(51) Int. Cl.
*A61F 2/16*    (2006.01)
(52) U.S. Cl.
CPC .......... *A61F 2/1648* (2013.01); *A61F 2/1632* (2013.01)
(58) Field of Classification Search
CPC .............................. A61F 2/1632; A61F 2/1648

USPC ... 623/6.34, 4.11, 6.11, 6.25, 6.27, 6.3–6.32, 623/6.38–6.43, 6.46, 6.2, 6.18, 6.33
See application file for complete search history.

(56) References Cited

U.S. PATENT DOCUMENTS

| 583,790 | A |   | 6/1897 | Cross |  |
|---|---|---|---|---|---|
| 3,305,294 | A | * | 2/1967 | Alvarez | 351/169 |
| 3,583,790 | A |   | 6/1971 | Baker |  |
| 4,022,855 | A | * | 5/1977 | Hamblen | 264/1.38 |
| 4,409,691 | A | * | 10/1983 | Levy | 623/6.34 |
| 4,435,856 | A | * | 3/1984 | L'Esperance | 623/6.34 |
| 4,666,445 | A | * | 5/1987 | Tillay | 623/6.18 |
| 4,842,600 | A | * | 6/1989 | Feaster | 623/6.42 |

(Continued)

FOREIGN PATENT DOCUMENTS

| EP | 0162573 A2 | 11/1985 |
|---|---|---|
| WO | 2004000171 A1 | 12/2003 |

*Primary Examiner* — Corrine McDermott
*Assistant Examiner* — Joshua Levine
(74) *Attorney, Agent, or Firm* — The Webb Law Firm

(57) ABSTRACT

The invention relates to an artificial intra ocular lens of variable optical power, comprising at least two optical elements which can be shifted relative to each other in a direction extending perpendicular to the optical axis wherein the optical elements have such a shape that they exhibit, in combination, different optical powers at different relative positions. This results in a construction which has such a low weight that it is applicable as an intra ocular lens of adjustable optical power. According to a first preferred embodiment the lens comprises positioning means the optical elements in the eye and driving means, which can be operated by the user to execute a movement of at least one of the optical elements relative to the other optical element. This embodiment can be used to correct the accommodation function.

8 Claims, 3 Drawing Sheets

(56) References Cited

U.S. PATENT DOCUMENTS

| | | | |
|---|---|---|---|
| 4,994,082 A * | 2/1991 | Richards et al. | 623/6.32 |
| 5,354,334 A | 10/1994 | Ismankulov | |
| 5,443,506 A * | 8/1995 | Garabet | 623/6.13 |
| 5,496,366 A * | 3/1996 | Cumming | 128/898 |
| 5,674,282 A * | 10/1997 | Cumming | 623/6.44 |
| 5,824,074 A * | 10/1998 | Koch | 623/6.34 |
| 6,113,633 A * | 9/2000 | Portney | 623/6.32 |
| 6,120,148 A * | 9/2000 | Fiala et al. | 351/161 |
| 6,197,058 B1 * | 3/2001 | Portney | 623/6.34 |
| 6,231,603 B1 * | 5/2001 | Lang et al. | 623/6.37 |
| 6,454,801 B1 * | 9/2002 | Portney | 623/6.34 |
| 6,616,691 B1 * | 9/2003 | Tran | 623/6.11 |
| 2002/0091442 A1 * | 7/2002 | Snyder | 623/6.12 |
| 2004/0158322 A1 * | 8/2004 | Shen | 623/6.33 |

\* cited by examiner

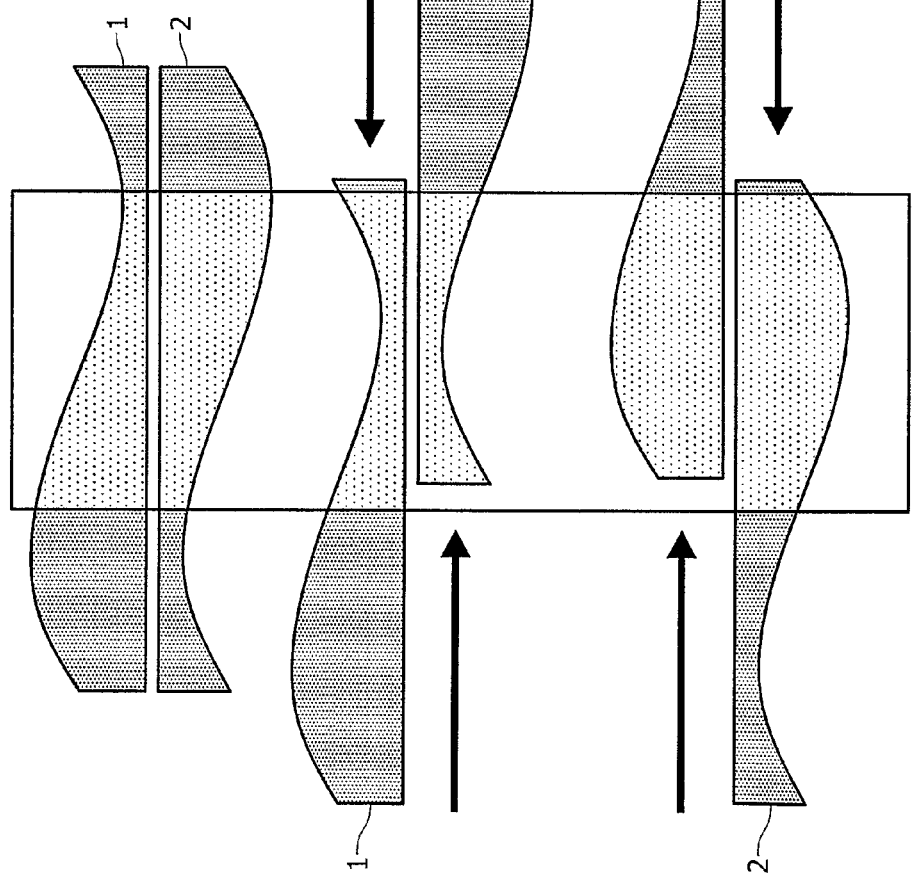

TWO OPTICAL ELEMENTS WHICH, IN COMBINATION, FORM A LENS OF VARIABLE OPTICAL POWER FOR APPLICATION AS AN INTRAOCULAR LENS

BACKGROUND OF THE INVENTION

1) Field of the Invention

The invention concerns an intra ocular lens.

2) Description of the Prior Art

Such a lens is generally known. Artificial intra ocular lenses are used inter alia to treat cataracts to replace the opaque cataracterous natural lens of the eye. These intra ocular lenses have a fixed optical power. The optical power of the intra ocular lens can become sub-optimal due to changes in the optical characteristics of the eye, for example changes due to aging. The optical power has to be corrected by either spectacles or surgical replacement of the intra ocular lens by a new intra ocular lens.

Also, due to the fixed optical power the natural accommodation function of the eye will be lost. As a consequence the person in which the intra ocular lens is implanted will have to rely on spectacles to aid accommodation.

We refer to U.S. Pat. No. 3,305,294 from which the principle of variable optical power of such a lens is known, albeit in inter alia spectacles. This document is hereby incorporated herein by reference. Also U.S. Pat. No. 3,583,790 is noted which further describes the optics.

Subsequently the workings of the eye and the background of the invention will be described. When a person looks at an object the object will reflect light which reaches the eye and this light results in a sharp image of the object on the retina after the light has passed through an optical system which includes the cornea, several eye-chambers which are filled with fluids and the lens of the eye. For objects close-by the total optical power of the eye needs to be larger compared to objects at a distance. The lens in the eye is capable of changing this optical power. The elastic natural lens is situated in the capsular bag. This elastic capsular bag can be stretched by relaxation of the ciliary muscle of the eye, which flattens the lens, which in turn results in an eye which focuses on a distance. When the ciliary muscle contracts the capsular bag will relax and the natural lens will resume its natural most spherical shape, which results in an eye which focuses near-by. Accommodation is this process of focusing the eye for sharp images of objects at various distances.

When a patient develops a cataract the natural lens becomes hard and opaque and the patient becomes blind. Cataracts are treated by replacement of the natural lens by an artificial lens in routine surgery. The patient regains vision, but will have a life-long need for spectacles for sharp vision in a distance, sharp vision nearby or both. The current intra ocular lenses do not react adequately to contraction and relaxation of the ciliary muscle—the eye focuses only at one distance or can focus only at a limited range. Virtually all present cataract intra ocular lenses are non-accommodative with a fixed focal length. It is an object of the invention to replace the opaque lens of a cataract patient with a new clear lens of excellent optical quality and restore the accommodation.

Virtually everyone becomes presbyope ("reading-farsighted") after the age of 45. The natural lens becomes hard, less elastic and does not resume its natural most spherical shape when the ciliary muscle contracts. Presbyopes are in need of reading-spectacles for focusing at nearby objects. Later pre-cataracts can develop which further degrade vision. Presbyopes would be greatly aided by a high quality accommodating intra ocular lens which would relieve them of the reading-spectacles, would restore the overall quality of their vision and would prevent cataracts. It is a further object of this invention to replace the presbyopic low quality and hardened natural lens by a clear lens of excellent optical quality which also restores accommodation.

The desired basic power of an artificial lens to be implanted is often difficult to estimate by the eye surgeon, especially when it concerns measurements on a catacterous eye. The intra ocular lens has preferably a dioptre value which results in an eye which is focused at the far distance. No current intra ocular lens can be adjusted once in the eye. It is a still further object of this invention to provide an intra ocular lens which can be adjusted post-operatively by a shift of the optical elements to a new resting state by shortening or lengthening the haptics or other components by light, laser light, ultrasonic energy, magnetic or mechanical energy or force.

Traditionally the refractive correction of the eye is accomplished with spectacles and contact lenses, but recently also by reshaping the cornea with lasers. However, one can also insert a refractive intra ocular lens (also: "refractive lengths", "corrective intra ocular lens", "phakic lens", "refractive phakic implant lens" or "claw lens") just behind the cornea, in the anterior or posterior chamber of the eye. This refractive lens relieves the patient of the need for eye glasses and the refractive intra ocular lens functions in conjunction with the natural lens which performs the accommodation function. These refractive intra ocular lenses are now manufactured, marketed and implanted routinely in the anterior chamber of the eye, on the iris, behind the iris or near the anterior side of the capsular bag. However, the optical power of these refractive lenses needs often to be adjusted or re-adjusted after implantation or the patient remains in need of spectacles. The refractive lenses can be removed in a second surgery and replaced with a new set of refractive intra ocular lenses. Intra ocular lenses which can be adjusted and/or re-adjusted do not yet exist. It is a still further object of the invention to provide lenses which are adjustable and/or re-adjustable, also post-implant, in the eye, concerning the basic dioptre power or accommodation range. This adjustment results from a shift of the optical elements of the lens to a new resting state.

At present accommodating intra ocular lenses are in development with few products newly on the market and these include:

- a first generation accommodating intra ocular lenses with a single spherical lens and hinges which translate the force of the ciliary muscle, which is perpendicular to the optical axis in a movement forward of the intra ocular lens along the optical axis, or
- the second generation accommodating intra ocular lenses, mostly experimentally to date, with a mode of action similar to the first generation, but of which an overly high dioptre value of the moving lens is corrected by a static negative lens which typically is situated near the posterior side of the capsular bag, or
- several experimental intra ocular lenses which include lenses made of soft masses of polymers which mimic the natural lens or encapsulated soft masses of polymers which mimic the natural lens.
- There are no intra ocular lenses in development which are of a kind described in accordance with the present invention below.

To avoid these disadvantages there is a need for intra ocular lenses which aid accommodation and are adjustable.

SUMMARY OF THE INVENTION

This aim is reached in that the lens comprises at least two optical elements which can be shifted relative to each other in a direction extending perpendicular to the optical axis wherein the optical elements have such a shape that they exhibit in combination, different optical powers in different relative positions.

This results in a construction which has such a low weight that it is applicable as an intra ocular lens of adjustable optical power.

According to a first preferred embodiment the lens comprises positioning means the optical elements in the eye and driving means, which can be operated by the user to execute a movement of at least one of the optical elements relative to the other optical element. This embodiment can be used to correct the accommodation function.

Another embodiment provides the feature that the driving means are adapted to be connected to the ciliary muscle of the eye. Without further intervention the system can be driven by the present natural accommodation functions of the eye.

Yet another embodiment provides the feature that the optical elements comprise adjusting means to adjust the resting position of the optical elements. This design can be applied to adjust and/or re-adjust the optical power of the lens to changes of the optical characteristics of the eye.

Other attractive embodiments appear from the other subclaims.

BRIEF DESCRIPTION OF THE DRAWINGS

The accompanying figures show:

FIGS. 1a-1c: the basic principle of a lens consisting of two optical elements which, in combination, form a lens of variable optical power

FIG. 2b: a schematic plan view of the accommodating lens depicted in FIG. 2a;

FIG. 5b: a cross sectional view of the accommodating lens depicted in FIG. 5a;

FIG. 7b: a cross-sectional view of the accommodating lens depicted in FIG. 7a.

DETAILED DESCRIPTION OF THE PREFERRED EMBODIMENTS

Figure 2A:
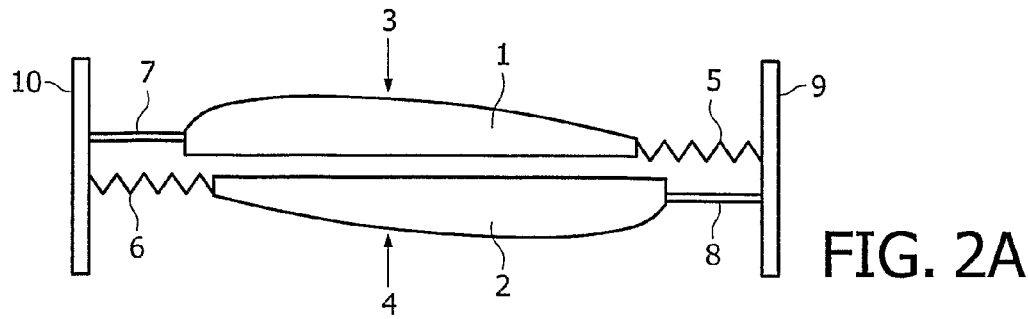
FIG. 2a: a schematic side view of an accommodating lens according to a first embodiment.

Initially the principle on which these inventions are based will be described. FIG. 1 shows two optical elements 1,2 with specific optical surfaces 3, 4, which elements 1,2 may be shifted laterally which results in a lens of variable optical power over the central area where the optical elements 1, 2 overlap. This principle is described in U.S. Pat. No. 3,305, 294.

This lens effect can be accomplished by a "saddle shaped" surface 3, 4 on one or on both sides of the optical elements 1, 2, which is a known principle. It is however also possible to make use of diffraction structures or diffraction gratings, for instance according to the GRIN principle. Herein flat optical elements containing materials with different refractive indices are used. Although a mutual translation of the optical elements 1, 2 is now envisaged, the elements can also be designed such that the lens effect is accomplished by rotation of the optical elements 1,2 relative to each other. The elements can be with or without a connection between the optical elements 1,2. Variable lenses of such two optical elements have been used occasionally as telescope and camera lenses in the past. The use of such a lens consisting of two optical elements as an intra ocular lens is completely new for applications as accommodating intra ocular lenses.

The lenses can fulfil the function of an adjustable and re-adjustable artificial intra ocular lens or of an adjustable and re-adjustable accommodating artificial intra ocular lens. Both applications offer significant advantages over current intra ocular lenses.

The basic designs of the intra ocular lenses include:

Two optical elements 1, 2 which are positioned on top of each other or with a space between each other and which compose the optical part of a construction which can further be composed of supporting components, elastic or non-elastic which keep the optical elements in the correct configuration and components which position the optical elements in the eye and so called haptics which are the clamps which are at one end connected to the optical elements and at the other end connect the optical construction to parts of the eye and additional components such as intraocular clamps, intraocular rings, optical filters and intra ocular envelopes which can be part of the construction depending on the application and depending on the condition or needs of the patient or eye, or the application of the lens accommodating intra ocular lens for treatment of cataract or presbyopia or as a non-accommodating refractive adjustable lens of a fixed optical power. The optical elements can be, including but not exclusive round, ellipsoidal, square, rectangular or combining shapes of the foregoing and with square or round edges or combinations thereof on both optical elements or haptics, clamps or supporting components depending on the needs and medical and optical condition of the individual eye and of which the lens comprises two optical elements according to claim 1 with or without connections between the optical elements including but not exclusive fixed connections, connections which allow a shift, elastic connections, hinges or connections which can move freely and of which the optical elements or other components of the optical system, being the haptics or other components can be changed the shape, relative position or the elastic characteristics or other characteristics by, including but not exclusive, light, laser-light, ultrasonic energy, mechanical energy and magnetic energy or a mechanical surgical interference to adjust the optical elements to a new resting state after implantation of the intra ocular lens ("post surgery") resulting in an adjustable intra ocular lens. Adjustable intra ocular lenses have significant advantages for the patient and surgeon and are not yet on the market.

The intra ocular lenses described in this patent share a number of advantages with the current intra ocular lenses—they can also be manufactured with standard procedures from standard and registered intra ocular lens materials such as various acrylates and silicones, can be rolled or folded for implantation through a micro-incision in the eye during standard cataract, presbyope or refractive surgery, do not give reason to expect increased risk for post cataract opacification ("PCO") and can be fitted with color-filters for color correction and/or UV protection.

The intra ocular lenses described in this patent are also, in contrast to virtually all other intra ocular lenses accommodating (for cataracterous and presbyopic patients), or of fixed optical power and adjustable (for refractive applications), both of which lens types can be adjustable or re-adjustable. A pre-surgery choice of accommodative power of <−10 dioptres up to >+10 dioptres or part of these ranges, which range can be added to the fixed power of the lens. (Example: Typical intra ocular lenses have a fixed standard power in the range of +20 to +30 dioptres for focusing the eye at the distance, with details depending on the needs of the particular eye, which can be determined pre-surgery. To this base optical power a +3 to +5 dioptres are added in accommodative power for focusing nearby, for example for reading.). The intra ocular lenses can be adjustable pre-surgery (during manufacturing of the intra ocular lens, or just before implantation outside the eye) and re-adjustable post-surgery (after implantation, inside the eye, directly following implantation, shortly after the implantation or long after the implantation) by adding optical power (adding dioptres) or subtracting optical power (subtracting dioptres) or by shifting the range of accommodation by shifting the optical elements to a new fixed resting state (for focusing at the distance, for refractive intra ocular lenses) or a new resting state (for focusing at the distance, for the accommodative type intra ocular lens).

The advantages outlined above are important for the patient with a cataract by restoring the accommodation and providing the opportunity to adjust the resting state of the intra ocular lens but also for the patient with a refractive error and by which the lens does not correct sufficiently and has to be replaced. The intra ocular lenses described in this patent are expected to increase the overall market for intra ocular lenses because new applications arise, especially for presbyopic patients for which no suitable accommodating intra ocular lenses are currently available.

The new accommodating intra ocular lens described in this patent restores the accommodation because the ciliary muscle in the eye changes the diameter of the capsular bag. This, in turn, changes the relative position of the optical elements of the accommodative intra ocular lens by shifting the optical elements to another position relative to each other, a result also affected by the natural elasticity of the capsular bag and fixed and elastic connections of the intra ocular lens and haptics. The design is such that a lens of the desired optical power results in the overlapping area of the two optical elements from contraction of the ciliary muscle to correct the optical power for the individual eye.

In addition, the optical elements, or the haptics, or part of the haptics or other supporting components can be changed in shape or size before or after the implantation by energy, which can include light, laser light, ultrasound or magnetic energy from outside the eye (and with, for example, micro-magnets included in the haptics or other components of the intra ocular lens) and applied from outside the eye via the cornea or via the sclera or by mechanical manipulation from outside the eye or by mechanical manipulation inside the eye.

Figure 2B:
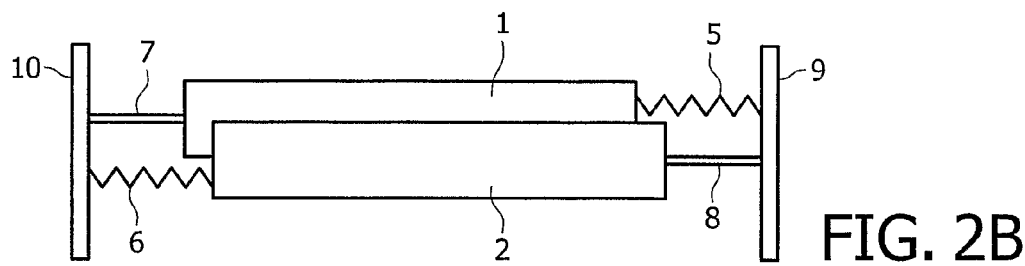

FIGS. 2a and 2b depict an optical system with the two optical elements 1,2 with each an elastic haptic 5, 6 and a non-elastic haptic 7, 8. The elastic haptic 5, 6 of one element 1, 2 is connected with the non-elastic haptic 7, 8 of the other element 2, 1 through an anchor 9, 10 and this connecting anchor 9, 10 connects the optical system directly to a part of the capsular bag of the eye or to a supporting component which in turn connects to a part of the capsular bag of the eye. The haptics 5-8, the connecting anchors 9, 10 or any other part of the optical system can be adjustable and/or re-adjustable.

Figure 3:
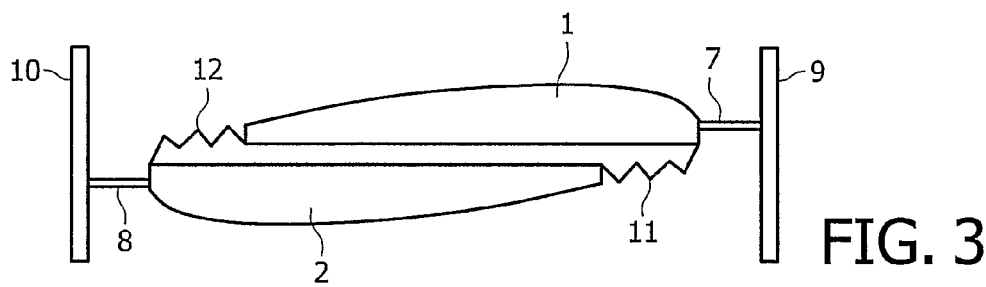
FIG. 3: a schematic view of an accommodating lens according to a second embodiment.

FIG. 3 depicts a second embodiment of an accommodating lens. This optical system has the two optical elements 1, 2 joined by elastic connections 11, 12, which may be formed by an elastic membrane, membranes, or several singular connections. Both elements have at opposite sides a non-elastic haptic 7, 8, which connects the system to the capsular bag. The haptics 7, 8, 11, 12, the connecting anchors 9,10 or part of the optical system can be adjustable and/or re-adjustable. The optical system of the second embodiment a refractive lens comprises two optical elements which can be connected by elastic connections, and which each have at one side one or more long non-elastic haptics.

Figure 4:
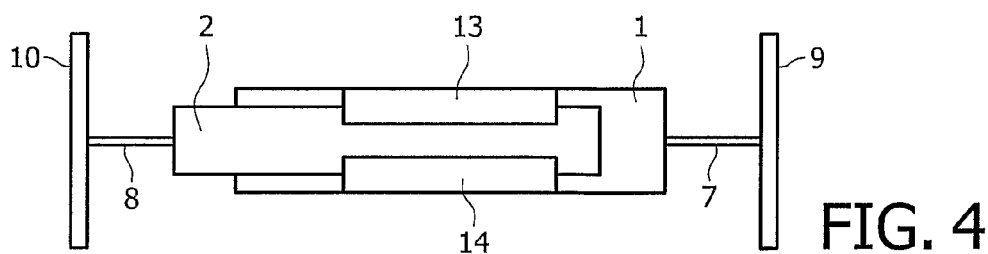
FIG. 4: a schematic view of an accommodating lens according to a third embodiment.

FIG. 4 shows a third embodiment of an accommodating lens. The optical system depicted in this figure comprises two optical elements 1, 2 which each have a non-elastic haptic 7,8. The optical elements 1, 2 both have, at their rims along the central area a short and small or wider clamp 13, 14 which can embrace, at the rim, in part, the other element 1,2, or only one of the optical elements 1, 2 has clamps at both sides to embrace the other optical element 1,2. The clamps 13, 14 leave sufficient space as not to hamper a sliding movement of the optical elements 1, 2 during the accommodative and dis-accommodative process. The haptics 7, 8 connect the optical system 1, 2 directly to a part of the capsular bag of the eye or to a supporting component 9, 10 which in turn connects to the capsular bag of the eye. The haptics 7, 8, the connecting anchors 9, 10 or any part of the optical system can be adjustable and/or re-adjustable. The optical elements both have, at the rim, along the central area a short and small or wider clamp with which the elements can be clamped together, or one of the optical elements has clamps at both rims to embrace the other element. The clamps leave sufficient space as not to allow a free sliding movement of the optical elements unless a certain force is applied. The haptics, the connections or part of the optical system can be adjustable and/or re-adjustable.

Figure 5A:
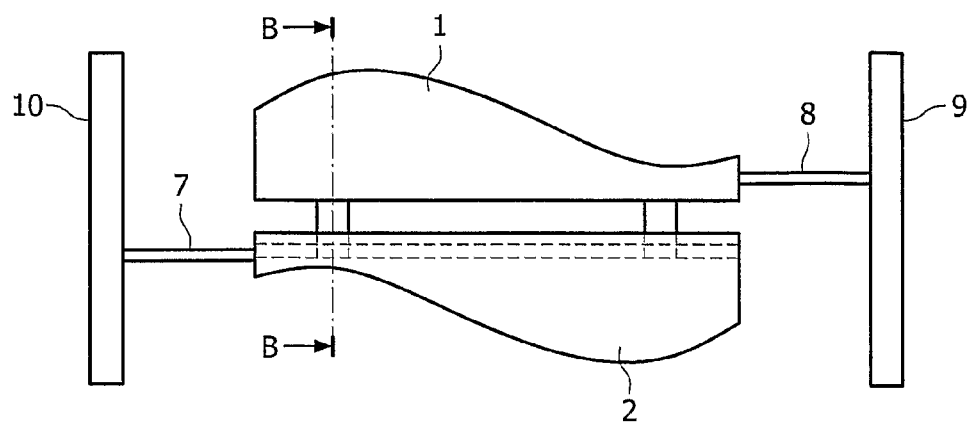
FIG. 5a: a schematic view of an accommodating lens according to a fourth embodiment.
Figure 5B:
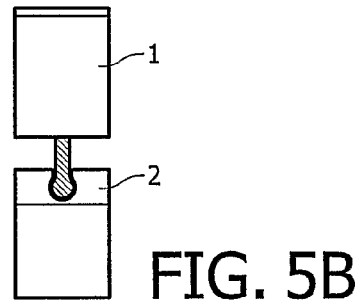

FIG. 5a depicts a fourth embodiment of the invention. This embodiment comprises two optical elements 1, 2 which each have a non-elastic haptic 7, 8. The first optical element 1 is connected with two substantially mushroom shaped pins 15, 16 which adapted to slide within a groove 17 provided in the other optical element 2. This also appears from FIG. 5b. The dimensioning of the groove 17 and the pins 15, 16 is such that a sliding movement of the optical elements 1, 2 relative to each other during the accommodative and dis-accommodative process is not hampered. Instead thereof, both optical elements may be provided with a groove and a mushroom shaped pin, so that the a symmetrical construction is obtained. The haptics 7, 8, 9, 10 connect the optical system 1, 2 directly to a part of the capsular bag of the eye or to a supporting component which in turn connects to the capsular bag of the eye. The optical elements have each, at the rim, along the central area at one rim a pin and at the other rim a groove to accomplish a pin-in-groove connection, or both elements have several pin and groove structures which connect the optical elements with connection which has insufficient space to allow the optical elements to shift freely unless a certain force is applied. The haptics attach the system to the eye. The haptics, the connection or part of the optical elements are adjustable and/or re-adjustable.

Figure 6:
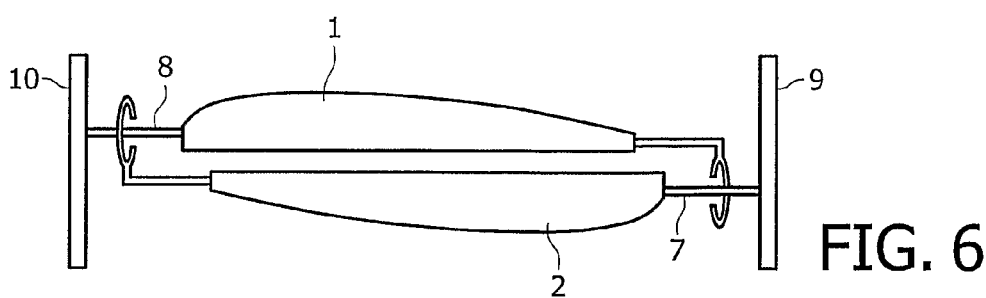
FIG. 6: a schematic view of an accommodating lens according to a fifth embodiment.

The fifth embodiment of an accommodating lens is illustrated in FIG. 6. The optical system has the two optical elements 1,2 which can be connected by elastic connections, and which each have at one side one or more long non-elastic haptics 7, 8 and at the other side one or more shorter non-elastic haptics 19, 20 which have an open or closed ring or clamp 21, 22 which connects the short haptic 19, 20 of any one element to the longer haptic 7, 8 of the other element allowing sufficient space at the connections point for a free movement during the accommodative and dis-accommodative process. The long non-elastic haptics 7, 8 connect the system to the capsular bag or to a supporting component or anchor 9, 10 which in turn connects the system to the capsular bag. The haptics, the connections or part of the optical system can be adjustable and/or re-adjustable.

Figure 7A:
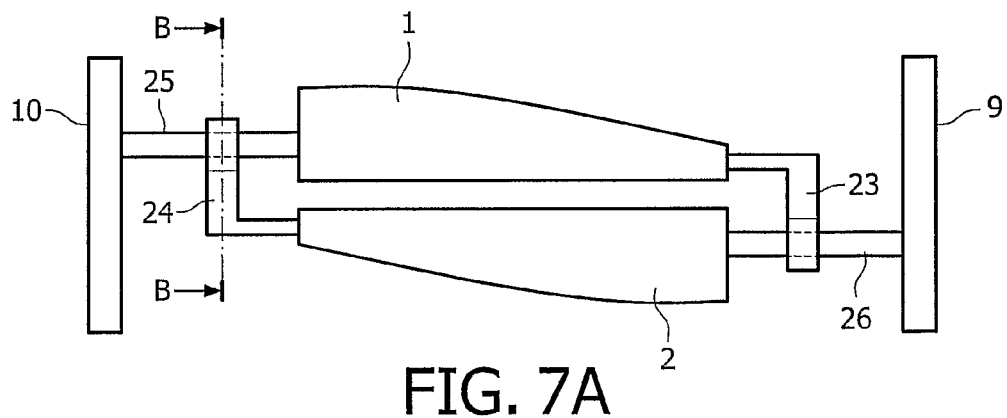
FIG. 7a: a schematic view of an accommodating lens according to a sixth embodiment.
Figure 7B:
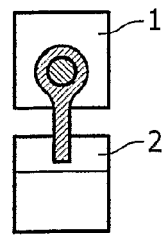

A sixth embodiment of an accommodating lens is schematically depicted in FIGS. 7a and 7b. This embodiment comprises the two optical elements 1,2 which each have at one side a short elastic strap 23, 24 and a long elastic strap 25, 26 at the other side. The shorter elastic straps 23, 24 embrace the longer strap-shaped haptics 25, 26, which connect the system to the capsular bag or to supporting components which in turn connect the optical system to the capsular bag. The haptics, the connections or part of the optical system can be adjustable and/or re-adjustable.

The optical system of the first design of a refractive lens has two optical elements which are connected at both sides. The optical elements have haptics at opposite sides which connect the system to a part of the eye. The haptics, the connections or part of the optical system can be adjustable and/or re-adjustable.

The refractive adjustable and/or re-adjustable lenses can also have different designs, namely according to the designs of accommodating lenses, but without allowance for free movement—in refractive lenses the optical elements can not be shifted by natural forces in the eye but only by external, non-natural forces.

Higher order refractive errors such as cylindrical errors and, even higher order, asymmetrical errors are likely to be corrected with the intra ocular lenses described in this patent, or can be corrected by additional intra ocular lenses, or can be corrected by an additional third optical element that does not shift relative to the other optical elements. With accommodating intra ocular lenses this third element can be part of an envelope or intra ocular ring.

The invention claimed is:

1. An artificial intraocular lens of variable optical power comprising at least two optical elements of which at least one can be shifted relative to any other element in a direction extending perpendicular to an optical axis when in an eye,
    wherein the shape of the surface of at least two optical elements includes a saddle-shaped surface according to the formula $t=A(xy^2+x^3/3)$, with t being the lens thickness of the optical element in the direction of the optical axis, x the coordinate in the direction of the motion of the optical elements, y the coordinate in the direction perpendicular to the optical axis and to the x-direction, and A a constant,
    wherein the optical elements, in combination, form a lens of which the optical power varies depending on the relative position of the optical elements,
    wherein each of the optical elements is affixed to an elastic haptic on one side thereof and to a non-elastic haptic on an opposite side thereof,
    wherein the elastic haptic affixed to each optical element is connected to one non-elastic haptic of another optical element through a connecting anchor, such that the lens comprises at least two separate connecting anchors,
    wherein a direction of relative shifting of the optical element is parallel to an imaginary line connecting the separate connecting anchors.

2. The artificial intraocular lens according to claim 1, comprising driving means adapted to execute a movement of at least one of the optical elements relative to the other element.

3. The artificial intraocular lens according to claim 1, comprising adjusting means wherein the adjusting means are adapted to provide adjustment of the resting state of the artificial intraocular lens.

4. The artificial intraocular lens as claimed in claim 1, wherein each connecting anchor is adapted to be connectable to a part of the capsular bag of the eye.

5. The artificial intraocular lens according to claim 1, wherein the lens is adapted to provide refractive correction of the base optical power of the eye.

6. The artificial intraocular lens according to claim 1, wherein the lens is adapted to provide correction of higher order refractive errors.

7. The artificial intraocular lens according to claim 1, wherein the lens is an accommodating intraocular lens.

8. The artificial intraocular lens according to claim 1, wherein the lens is an adjustable intraocular lens.

* * * * *